United States Patent [19]

Hamano et al.

[11] Patent Number: 5,302,391

[45] Date of Patent: Apr. 12, 1994

[54] METHOD OF ENHANCING THE ABILITY OF CATTLE AND SWINE TO RESIST AUJESKY'S DISEASE

[75] Inventors: Atsushi Hamano, Ibaraki; Megumi Ogawa; Takashi Sasaki, both of Sakura, all of Japan

[73] Assignee: National Federation of Agricultural Cooperative Associations, Tokyo, Japan

[21] Appl. No.: 836,204

[22] Filed: Feb. 18, 1992

Related U.S. Application Data

[63] Continuation of Ser. No. 634,335, Dec. 26, 1990, abandoned.

[30] Foreign Application Priority Data

Dec. 27, 1989 [JP] Japan ................... 1-340728

[51] Int. Cl.$^5$ ............................. A61K 35/78
[52] U.S. Cl. .................. 424/195.1; 424/528
[58] Field of Search ............ 424/195.1, 528; 514/783

[56] References Cited

U.S. PATENT DOCUMENTS

| 196,916 | 11/1877 | Marshall | 424/195.1 |
| 412,837 | 10/1889 | Carnrick | 424/528 |
| 979,054 | 12/1910 | Bader | 424/528 |
| 3,408,201 | 10/1968 | Moyle | 424/528 |
| 4,140,805 | 2/1979 | Edwards | 426/429 |
| 4,264,583 | 4/1981 | Jandacek | 424/240 |
| 4,774,232 | 9/1988 | Szejtli | 514/58 |

FOREIGN PATENT DOCUMENTS

| 437321 | 3/1968 | Japan | 424/528 |
| 62-059214A | 3/1987 | Japan . | |

OTHER PUBLICATIONS

Steinmetz E. F. Codek Vegetabilis 1957 Amsterdam #59, 525, 941.

Rossoff I. S. Handbook of Veterinary Drugs Springer, N.Y. 1975 p. 245.

Reynolds J. Martindale 28th Ed 1982 London Pharmaceutical Press p. 652.

Dure J. A. CRC Handbook of Medicinal Herbs Boca Raton, Fla. 1974 p. 399.

*Primary Examiner*—Michael G. Wityshyn
*Assistant Examiner*—Ralph Gitomer
*Attorney, Agent, or Firm*—Keck, Mahin & Cate

[57] ABSTRACT

A method of enhancing the ability of cattle and swine to resist diseases caused by microorganisms which comprises the steps of adding an antimicrobial effective amount in a range of 0.01 to 0.2% by weight of bile powder to a livestock feed and administering the livestock feed prepared to the cattle and swine. The method may also comprise adding a pharmaceutical effective amount of one of the following: licorice, garlic or quillaja powders or extracts thereof to the livestock feed.

2 Claims, No Drawings

METHOD OF ENHANCING THE ABILITY OF CATTLE AND SWINE TO RESIST AUJESKY'S DISEASE

This application is a continuation of application Ser. No. 07/634,335, filed Dec. 26, 1990, now abandoned.

BACKGROUND OF THE INVENTION

The present invention relates to a livestock feed and a feed additive containing safe natural materials having a weight gain effect and an improving effect of the health of livestock.

There are many problems to be solved in the field of livestock breeding, one of which is an economical loss caused by various diseases of livestock due to a deterioration of a sanitary environment. As a countermeasure against livestock diseases, especially caused by microbes, there have been applied various additives in feed such as synthetic antimicrobial or antibiotic substances, and vaccinations in livestock farms, but they have not been working efficiently against the various infectious diseases of livestock except in a few cases. Also excessive medication sometimes cause a reduction of productivity due to the unexpected side effects of the additives. Accordingly, there has been a need for some safe and labor-saving disease preventing measure, because of depreciation of commercial value of livestock products due to residual medicines therein.

It is almost impossible to resolve all the diseases of livestock farms by using vaccination and antibiotic medicines. If it could be done, it would require a large amount of expense and medicine. Also, there is another problem to be resolved on the side effects of medicines and residual medicines in the products, when those medicines are widely used.

SUMMARY OF THE INVENTION

The present invention has been developed considering the above situation and provides a safe livestock feed and a feed additive resulting in an improvement of the health of cattle and swine and a high weight gain.

In order to carry out the above object, it has been found that a bile powder made from bile of livestock has an antimicrobial effect and that livestock feed containing bile powder or bile power and at least one of the following safe natural substances such as licorice (*Glycyrrhizae glabra*), licorice extract, garlic powder (powder of *Allium scorodoprasum* L. var. *viviparum Regal*) or quillaja extract improves the health of cattle and swine in a livestock farm contaminated with infectious microbes, resulting in an efficient growth of the livestock.

That is to say that the present invention relates to a livestock feed and feed additive containing bile powder, or at least one of a livestock feed and a feed additive containing bile powder and safe natural substances such as licorice, licorice extract for increasing disease resistance in cattle and swine, garlic powder or quillaja extract. These livestock feeds permit an improvement in the health and an effective growth of cattle and swine.

The bile powder can be obtained by directly pulverizing a bile element contained in cattle and swine gall bladders. Some of them are obtained by pulverizing them after extracting by an alcoholic extracting method. The principal ingredients contained in the aforementioned feed additives or feeds are cholic acid and deoxycholic acid. About 50% of cholic acids is contained in the bile powder.

Various refined products of cholic acid, containing a bile powder composition, have been used as medicine for human gall and a secretory accelerator of digestive enzymes and digestive fluids.

Licorice (*Glycyrrhizae glabra*) is a plant of pulse family, of which root is dried to be crushed or pulverized, and an extract thereof is a dark brown and adhesive extract having a particularly sweet and bitter flavor. However, its color varies according to the extracting process. Its main composition is a glycyrrhetic acid having a natural killer activity and an interferon inductivity, of which effect against human simplex herpes virus is widely recognized. The licorice powder and an extract thereof, absorbed in other foods, are added to livestock feed.

Garlic powder is made from garlic (*Allium Scorodoprasum* L. var. *viviparum Regal*) by drying and pulverizing the cloves. The garlic powder contains a glycoside of glycominar. When it is hydrolyzed, a kind of volatile oil containing sulfur and diaryldisulfide, an aromatic substance, is obtained. Also, the garlic powder contains allysine and has physiological activity such as an improvement of intestinal absorption of vitamin $B_1$.

Quillaja extract is a white to light yellowish brown powder or brown to dark brown pasty substance having a surface activity and has been used as a detergent and foaming agent for a long time. The main composition of the quillaja extract is an oligoglycoside such as triterpenoid and steroid. An extract of *Quillaja saponaria molina*, an evergreen tree of rose family, is mainly used to get the quillaja extract. When the quillaja extract is employed, the quillaja powder is mixed in a feed directly, and a pasty quillaja powder can be absorbed in a feed.

When the bile powder is mixed in a feed directly, its content must be chosen in the range of 0.01 to 1.0%, preferably in the range of 0.05 to 0.2% by considering the weight, day-old age and palatability of the cattle or swine.

When the bile powder is used as a feed additive, it is necessary to prepare a feed additive with more than 50% of bile powder first. A normal feed must be prepared so as to contain from 0.01 to 1.0% of bile powder, preferably 0.05 to 0.2% of bile powder by using the above feed additive with 50% of bile powder in accordance with the degree of microbial contamination of the respective livestock farm. For example, when a feed additive containing 50% of bile powder is used, the content of bile powder in the feed will be 0.1% when 0.2% of feed additive is added.

It is necessary to prepare a bile powder mixture on the basis of dry weight of the bile powder and other materials such as one part of bile powder to 0.1 to 1.0 of garlic powder, one part of bile powder to 0.001 to 0.05 of glycyrrhetic acid value of licorice or licorice extract, and one part of bile powder to 0.001 to 0.01 of triterpenoid (*Quillaja saponin*) value of quillaja extract.

Also other commercial materials sold as livestock feed or a feed additive for livestock can be used for preparing the bile powder mixture, which are selectively used considering the race, dayold age, weight, nutrition and palatability of the livestock. It is necessary for the livestock feed to contain vitamins and minerals, which may be mixed or added as well as other commercial materials.

The physical forms of the livestock feed and the feed additive for increasing disease resistance in cattle and swine may be of powder, grain or liquid form. They are used selectively in accordance with the feeding condition and installations of the farm.

The bile powder and grain thereof are so easy to handle as common feeds because of their aforementioned forms. When they are mixed into liquid feeds, there is another merit in improving an environmental condition preventing dust rising.

The bacteriastatic effect of bile against bacteria of livestock has been discovered by the present invention. In addition, an antivirus effect of the the bile powder was disclosed against a virus of Aujeszky's disease, one of virus causing various diseases spread on livestocks, against which there had been no cure. The antivirus effect of bile powder is more than that of cholic acids which has been extracted and refined from the bile powder. Therefore, it is more useful economically to use the bile powder directly in the livestock feed or the feed additive than to use the extracted and refined cholic acid.

The bile powder works directly on microbes such as virus and bacteria. Licorice, garlic powder, quillaja powder or their extracts activate to fortify physiological functions and cells of live bodies, especially immunocyte, and indirectly attributes to the improvement of the health, and weight gain effect of cattle and swine.

Brief Description of the Invention

The livestock feed and feed additive for increasing disease resistance in cattle and swine and feed additive according to the present invention are composed of safe natural substances such as bile powder, licorice, garlic powder and quillaja powder. Therefore, they are harmless to animals and contribute to improve the health of cattle and swine and to improve the weight gain effect.

Hereinafter, the effect of the present invention will be described in detail referring to some examples of the preferred embodiment as follows, by which the concept of the present invention will not be limited.

EXAMPLES

EXAMPLE No. 1

The bile powder prepared from freezing and drying the bile of cattle and swine was dissolved in PBS (phosphate buffer saline solution) and sterilized through a milipore filter of 0.45 μm. Then, the content of the bile powder was adjusted to 0, 0.03, 0.06, 0.125, 0.25, 0.5, and 1.0%. The bile-PBSs were mixed equally with a swine Aujeszky's disease virus solution ($8.5 \times 10^8$ $PFU/ml$) previously prepared and incubated at 37° C. for 60 minutes. Then, the mixture was diluted 100 times in MEM (Eagle's minimum essential medium) solution. Then it was applied on CPKs (cells of the piglet kidney) and its effect was evaluated after 5 days. The content, at which CPE (cytopathic effect) was not observed was evaluated as effective.

The results of the evaluation are shown in Table 1 below.

TABLE 1

| Antivirus Effect of the Bile Powder | | | | | | | |
|---|---|---|---|---|---|---|---|
| | content of bile powder | | | | | | |
| | 0 | 0.03 | 0.06 | 0.125 | 0.25 | 0.5 | 1 (%) |
| bile powder of cattle | + | + | + | − | − | − | − |
| bile powder of swine | + | + | + | − | − | − | − | where +: CPE observed (ineffective)
−: CPE not evaluated (effective)

The antivirus effect of the bile powder prepared from cattle and swine biles was confirmed.

EXAMPLE NO. 2

The bile powder prepared from freezing and drying bile of cattle and swine was solved in PBS (phosphate buffer saline) and filtrated through a milipore filter of 0.45 μm. Then, the content of the cholic acid was adjusted to 0, 0.0125, 0.025, 0.05, 0.1, 0.2, and 0.4% based on the total quantity of the cholic acid.

The bile-PBS adjusted based on the cholic acid quantity was mixed equally with a Aujeszky's virus solution ($8.5 \times 10^8$ $PFU/ml$) previously prepared and incubated at 37° C. for 60 minutes. Then, the mixture was diluted 100 times in MEM solution. Then, it was applied on CPKs (cells of the piglet kidney) and its effect was evaluated after 5 days. In the same manner, the values of deoxycholic acid and sodium cholic acid were adjusted and its effect was compared with the same of the bile powder.

The content, at which CPE (cytopatic effect) was not observed was evaluated as effective.

The results of the evaluation are shown in Table 2 below.

TABLE 2

| Comparison between the antivirus effects of the bile powder and the cholic acids | | | | | | |
|---|---|---|---|---|---|---|
| | content of cholic acid | | | | | |
| | 0 | 0.0125 | 0.025 | 0.05 | 0.1 | 0.4 (%) |
| bile powder of swine | + | + | + | − | − | − |
| bile powder of cattle | + | + | + | − | − | − |
| sodium deoxycholic acid | + | + | + | − | − | − |
| sodium cholic acid | + | + | + | + | − | − | where +: CPE observed (ineffective)
−: CPE not observed (effective)

EXAMPLE NO. 3

The bile powder prepared from freezing and drying bile of swine was dissolved in triptosoy medium solution and filtrated at a high temperature. Then the content of the bile powder was adjusted to 0, 0.5 and 1.0%.

Staphylococcus aureus 209P solution, which had been prepared previously, was inoculated by a platinum needle on 3 ml of triptosoy medium solution containing bile powder in test tubes and incubated at 37° C. Its OD (optical density) value (wave length: 600 nm) was measured periodically with burbidmeter so as to evaluate growth of the microbe. The OD value was 0.8 in 0% solution of bile powder, 0.5 in 0.5% solution of bile powder and 0.4 in 1.0% solution of bile powder after 10 hours of incubation. The OD value showed less microbe quantity in the higher content solutions of bile powder. Accordingly, a bacteriostatic effect of the bile powder against Staphylococcus aureus was confirmed.

Example No. 4

Feed additives A containing 50% of bile powder, B containing 50% of bile powder and 25% of garlic powder, C containing 50% of bile powder, 25% of garlic powder and 3% of licorice and D containing 50% of bile powder, 25% of garlic powder and 1% of quillaja extract were prepared and added to commercial feed for swine so as to be 0.2% of content.

Above feed additives were experimented at a livestock farm, which had shown such poor health conditions such as cough and diarrhea, and a low productivity. The feeds with additives A, B, C and D were each fed to 10 young swine of 15 to 20 days of age for 45 days. Then, their health conditions, feces conditions, weight gains and survival ratio were compared with those of another group of young swine fed with common swine feed without these additives for the same period. These results are shown in Table 3 below.

All which were fed with additives A to D, showed an improvement in health including diarrhea and weight gain effect when compared with those fed without the aforementioned additives.

TABLE 3

Clinical conditions and weight gains of young swine

| test group | weight gain | health condition (score) | diarrhea (score) | survival |
|---|---|---|---|---|
| control | 100 | 100 | 100 | 9/10 |
| ration with additive A | 112 | 75 | 75 | 10/10 |
| ration with additive B | 115 | 69 | 78 | 10/10 |
| ration with additive C | 114 | 65 | 78 | 10/10 |
| ration with additive D | 118 | 68 | 76 | 10/10 | where weight gain: average weight gain of 9 young swines considered as a score of 100 among the control.
health condition: each scored 1 for cough, snivel and poor appetite, and averages were calculated considering an average of 9 survived for 45 days as a score of 100.
diarrehea: each scored 1 for thin or pasty feces, and averages were calculated considering an average of 9 survived for 45 days as a score of 100.

What is claimed is:

1. A method of enhancing the ability of cattle and swine to resist Aujeszky's virus, comprising the steps of:
   a) adding 0.01 to 0.4% by weight of bile powder to a livestock feed; and
   b) administering the livestock feed prepared in step a) to said cattle and said swine.

2. The method of claim 1, further comprising the step of adding a pharmaceutical effective amount of one of the following selected from the group consisting of licorice, garlic and quillaja powders and extracts thereof to the livestock feed in step a).

* * * * *